US005859537A

United States Patent [19]
Davis et al.

[11] Patent Number: 5,859,537
[45] Date of Patent: Jan. 12, 1999

[54] ELECTROCHEMICAL SENSORS FOR EVALUATING CORROSION AND ADHESION ON PAINTED METAL STRUCTURES

[75] Inventors: Guy D. Davis, Baltimore; Chester M. Dacres, Columbia, both of Md.

[73] Assignee: Dacco Sci, Inc., Columbia, Md.

[21] Appl. No.: 724,753

[22] Filed: Oct. 3, 1996

[51] Int. Cl.$^6$ .............................. G01N 27/26; G01R 27/02
[52] U.S. Cl. ..................... 324/693; 324/700; 324/71.2; 204/404; 73/86
[58] Field of Search ................................. 324/693, 700, 324/71.2; 73/86; 204/404, 290 R

[56] References Cited

U.S. PATENT DOCUMENTS

| | | | |
|---|---|---|---|
| 4,806,849 | 2/1989 | Kihira et al. ........................ | 324/65 R |
| 5,221,893 | 6/1993 | Kondou et al. ..................... | 324/700 X |
| 5,338,432 | 8/1994 | Agarwala et al. ................... | 205/118 |
| 5,658,444 | 8/1997 | Black et al. ........................ | 204/415 |

OTHER PUBLICATIONS

Grandle et al. "Electrochemical Impedance Spectroscopy of Coated Aluminum Beverage Containers: Part 1–Determination of an Optimal Parameter for Large Sample Evaluation" Corrosion, vol. 50, No. 10, pp. 792+, Oct. 1994.

Simpson et al. "Evaluation of the Effects of Acidic Deposition on Coated Steel Substrates", Progress in Organic Coatings, vol. 20, pp. 199+ 1992.

Primary Examiner—Michael Brock

[57] ABSTRACT

A method for the early detection of electrochemical corrosion and coating degradation utilizing an inexpensive, in situ electrochemical metallic sensor for sensing coating and material degradation, particularly for materials such as aluminum 2024-T3, 7075, 6061, cold rolled steel samples, and coated metal structures such as automobiles, bridges, aircraft, and ships has been developed. The sensor utilizes AC Impedance or Electrochemical impedance spectroscopy (EIS) to acquire a precise, low-frequency impedance signature and is comprised of conductive ink deposited on a coating in the shape of the outline of a quadrilateral or other configuration. The resulting apparatus is comprised of a coated, metallic coupon used as a sensor, while a metallic grid electrode is deposited onto the steel coupon, thereby eliminating the need for a remote or counter electrode (i.e., reduction from a traditional, three-electrode system to a two-electrode system). Relying on the relatively lower impedance of the metallic grid electrode versus the coated metal, the electrodes are able to demonstrate a lower, interfacial impedance than the three-electrode testing system. This two-electrode approach eliminates the need for an electrolyte use in conventional, three-electrode AC Impedance testing and enables in-situ analyses of metallic and/or coating systems.

3 Claims, 19 Drawing Sheets

ELECTROCHEMICAL SENSORS FOR EVALUATING CORROSION AND ADHESION ON PAINTED METAL STRUCTURES

CROSS-REFERENCE

None

REFERENCE TO MICROFICHE APPENDIX, FOR COMPUTER PROGRAM LISTINGS

None

BACKGROUND OF THE INVENTION

1. Field of Invention

The invention pertains to the field of electrochemical corrosion chemistry. The corrosion sensor has potential applicability in a wide variety of painted metal structures, including highways and bridges, storage tanks, pipelines, locks and dams, towers, aircraft, vehicles, and ships. The most important benefit of this technology will be increased safety and reliability. The field-operational sensors will allow maintenance inspectors to detect the early stages of coating degradation/corrosion well before serious deterioration has occurred. Maintenance can then be scheduled based on the actual condition of the structure and need not be performed on an elapsed time schedule. Thus, the sensor could also potentially save maintenance cost in three ways:

Allowing an "as required" maintenance schedule

Initiating repairs before it becomes costly to perform them

Providing quantitative data regarding rates, and mechanisms of degradation.

Additionally, the ability to quantify corrosion rates and correlate laboratory and field exposure should become very important in the development and selection of new materials and processes. This added intelligence should enable structure lifetimes to be increased more economically than currently feasible.

In view of the tremendous economic and environmental cost of maintenance of infrastructures, the potential commercial applications of this technology to the construction and the military industries are enormous. Structure or hardware will have an increased lifetime utility with lowered lifetime maintenance cost. The commercial ramifications of electrochemical corrosion sensor development are also important to the insurance industry where the potential economic benefits could be substantial. Additionally, increased safety will be one of the most important benefits of this technology.

2. Description of the Related Art

An atmospheric in-situ sensor has been previously conceived for early detection of corrosion on painted steel.[1]

[1] Simpson, T. C. Moran, P. J., Hampel, H., Davis, G. D., Shaw, B. A., Arah, C. O., Fritz, T. L., and Zankel, K. L., "Electrochemical Impedance Measurements for Evaluating and Predicting the Performance of Organic Coatings for Atmospheric Exposure", Corrosion Testing and Evaluation: Silver Anniversary Volume, ASTM STP 1000, R. Baboian and S. W. Dean, Eds., American Society for Testing and Materials, Philadelphia, 1990, pp. 397–412.

The prototype sensor (1), (FIG. 1) as developed earlier, was a painted steel coupon approximately 1" by 1". A gold grid electrode (2) was deposited onto the steel coupon (3) by electron beam. This eliminates the need for a remote or counter electrode. Standard Electrochemical Impedance Spectroscopy (EIS) testing requires counter electrode because of the high impedance of the electrolyte. The monitor uses the fact that the gold grid electrode impedance is much lower than that of the coating on a metal. This results in low interfacial impedance between the electrodes and allows for a two electrode testing. This two electrode method enables an in-situ real time analysis of a metal/coating system, previously unavailable. Furthermore, it has been determined that the contact of the gold grid electrode with the coating does not accelerate or initiate corrosion of the coating at the contact point. Electrical lead wire (4) from the painted gold grid, acts as the reference and the counter electrode. Electrical lead wire (5) from the back of the sample acts as the working electrode. Electrical lead wire (6), from the front of the sample, acts as the counter electrode.

This technique was abandoned for a more practical approach using a low adhesive strength tape to lay the pattern of the grid. This technique proved to be simpler in design and allowed for easier application of the paint.

Silver paint was added to the scope of testing to provide another low cost alternative to the gold paint since there was concern that the carbon paint might not give accurate results due to its low electrical conductivity and suspected low abrasion resistance. The values for the measured electrical conductivity of the deposited electrodes are shown in Table 1.

TABLE 1

Current Resistance of Electrodes Taken from Opposite Corners of the Paint Grid.

| Electrode | Cure Temperature (C.) | Resistance (Ohms) |
|---|---|---|
| Gold (Au) | 50 | 4.5 |
| Gold (Au) | 80 | 2 |
| Silver (Ag) | 50 | .4 |
| Carbon | 50 | 675 |

It was found that the conductivity of the gold paint increases with cure temperature as supported by the specification sheet sent with the paint. However, there was concern that elevated cure temperatures might adversely alter the integrity of the coating. Therefore the lowest possible recommended cure temperature of 50° C. was chosen for all the paints.

Each coupon is comprised of two wires (13, 14), a painted electrode grid (10), an the coated sample (11). One wire (14) is bonded to the metal on the backside of the coupon and acts as the working electrode. The second wire (13) is bonded to the painted grid and acts as the reference and counter electrode. This two electrode approach have thus far been tested using the AC Impedance technique with success.

The following paints have been utilized for the electrodes:

Gold Paint (FIG. 2)

The gold paint used as a painted electrode (2) was the EPO-TED H81E form Epoxy Technology, Inc. The EPO-TEK H81E is a two component, gold filled epoxy. The paint is 100% solids (solventless) and will not outgass. In addition, the gold paint has high electrical conductivity resulting in low interfacial impedance between the gold and the coating. A drawback of the gold paint is the price.

Silver Paint (FIG. 3)

The silver paint used for painted electrodes is the 102-05F electrically conductive ink form Creative Materials, Inc. The 102-05F is one part 85% silver epoxy. The epoxy has high solvent resistance and has excellent adhesion and is resistant to scratching and abrasion. The silver epoxy is a lower cost alternative to the gold epoxy.

Carbon Paint (FIG. 4)

The carbon paint used for painted electrodes is the 104-18 electrically conductive ink from Creative Materials, Inc. The 104-18 is one part 85% carbon epoxy. Even though the electrical conductivity of the carbon is less than that of the gold paint, the carbon paint still has a much greater conductivity as compared the coating to which it will be applied. Results were similar to the gold paint electrodes. Carbon conductive paint is the most cost effective alternative to the gold paint electrodes. Carbon conductive paint is the most cost effective alternative to the gold and silver paints.

Nickel Paint

Nickel paint was used a electrode material because it is inexpensive and offers high conductivity. Its corrosion resistance is greater than that of the silver paint and its abrasion resistance is greater than the carbon paint.

SUMMARY OF THE INVENTION

An in-situ corrosion sensor, based on electrochemical impedance spectroscopy (EIS), is being developed to monitor the health of painted and bonded metal structures. EIS is commonly used to study corrosion of painted metals in the laboratory, but has not been suitable for field inspection as it typically requires immersion in an electrolyte with external counter and reference electrodes. The corrosion sensor eliminates the need for the electrolyte used in conventional three-electrode EIS and enables in-situ analyses of metal/coating systems. Two versions of the corrosion sensor are being tested: an attached electrode permanently applied to the topcoat and a probe which is pressed against the top coat during inspection. The impedance spectra obtained by the sensor and conventional laboratory measurements are identical, indicating that the sensor has negligible effect on the interaction of the painted metal with the environment and the sensor, itself, is stable with time and exposure. In immersion (acidic and saline solutions), humidity, and salt fog exposures, the measurements show that the coated metal degrades with a distinct signature having well defined regions of water uptake by the coating, incubation of corrosion, and intense interfacial degradation. Correlations were made between the EIS measurements and both ellipsometry and corrosion rate measurements determined by dc potentiodynamic polarizations. Accelerated exposure tests showed that the sensor readily detects the early stages of interfacial degradation well before any visual indication of corrosion appears. Similar results have been obtained from simple bonded structures. The ability to detect and quantify material degradation from its earliest stages in the laboratory and field suggests that one application would be the correlation of paint performance in accelerated test and field or ambient exposures. Another is to monitor critical structures to permit needs-based maintenance.

A Brief Ddescription of the Drawings, if any:

DESCRIPTION OF THE PREFERRED EMBODIMENT

The invention provides an in-situ sensor capable of detecting and monitoring corrosion of an actual structure from the earliest stages of deterioration. The sensor utilizes electrochemical impedance spectroscopy (EIS) for investigating corrosion and coating degradation. Methods of manufacturing such a sensor are also provided.

Referring to the drawings, FIG. 1 is a diagram of an atmospheric electrochemical monitor 1, with a gold grid electrode 2 and a painted on 2.54×2.54 cm coupon sample 3 with an electrical lead wire 4 attached to the gold grid (reference electrode) and an electrical lead 5 attached to the back of the coupon sample (working electrode) and an electrical lead wire 6 attached to the gold grid which acts also as a counter electrode.

FIG. 2 is a diagram of a painted coupon sample 1 with a gold painted electrode 2, an electrical lead wire 3 attached to the gold painted electrode (reference electrode), and an electrical lead wire 4 attached to the backside of the coupon (working electrode).

FIG. 3 is a frontal view of a silver paint electrode 2 on a painted coupon sample 1, with an electrical lead wire 3 (reference electrode) attached to the silver painted electrode and an electrical lead wire 4 attached to the back of the coupon sample 1 (working electrode).

FIG. 4 is a frontal view of a carbon paint electrode 2 on a painted coupon sample 1, with an electrical lead wire 3 (reference electrode) attached to the carbon paint electrode, and an electrical lead wire 4 attached to the cack of the coupon sample 1 (working electrode).

FIG. 5 is a plot of the corrosion process for painted aluminum 2024-T3 showing three (3) distinct areas of water uptake, incubation and corrosion.

FIG. 6 is a drawing of a sample with conductive ink electrode 2 deposited on a coated coupon sample 1 with an electrical lead wire 3 attached to the conductive ink electrode (reference/counter electrode) and an electrical lead wire 4 attached to the back of the coated coupon (working electrode).

Figure 10:
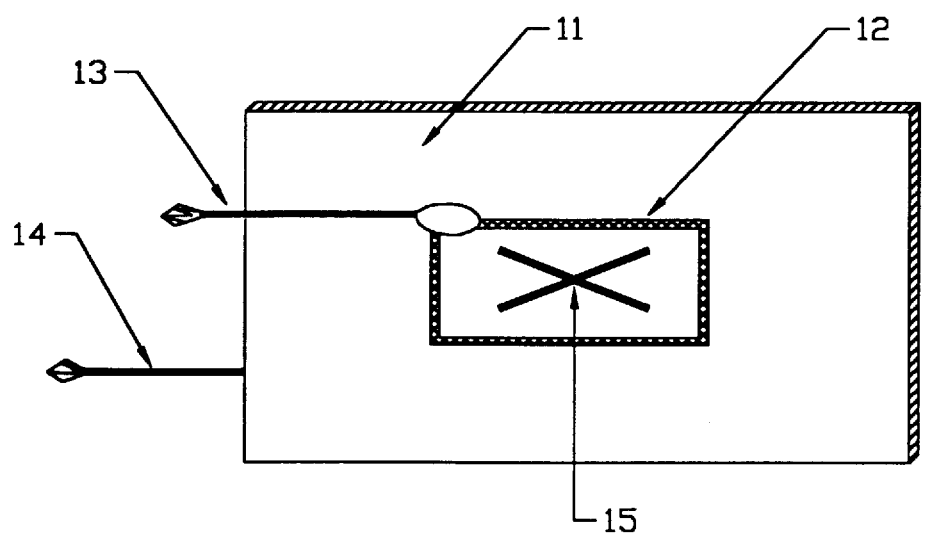

FIG. 10 is a diagram of a sample with an intentional (scribed) defect 5 on a coated coupon sample 1 with a conductive ink electrode 2 (reference/counter electrode) with an electrical lead 3 wire attached to the conductive ink electrode and an electrical lead wire 4 attached to the coated coupon sample (working electrode).

Figure 11:
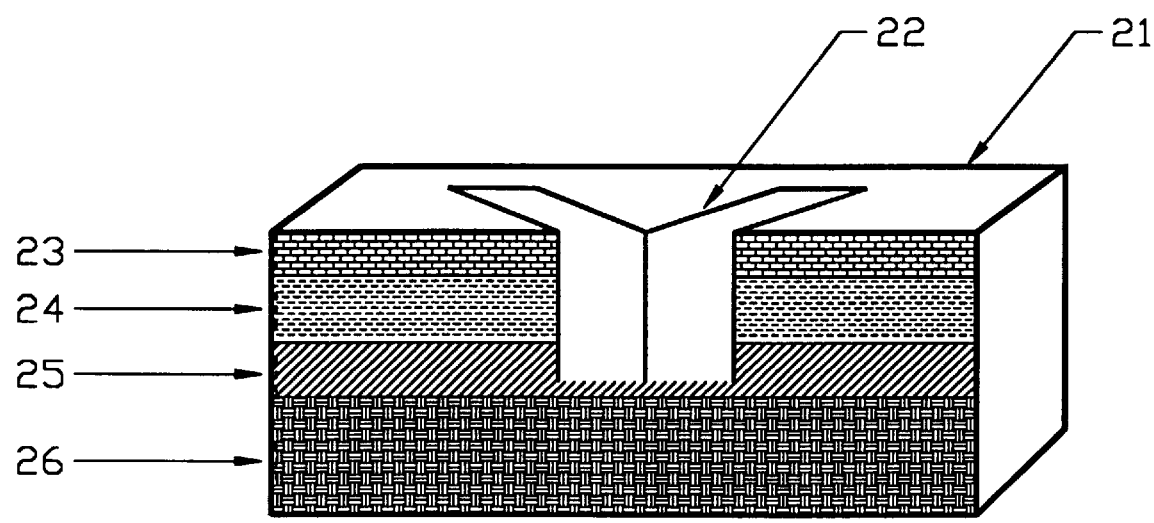

FIG. 11 is a diagram of a model of cross-section of sample 1 showing the defect 2 penetrating the urethane topcoat 3, the primer 4 and the oxide layer 5. The defect 4 stop at the aluminum substrate 6.

Figure 12:
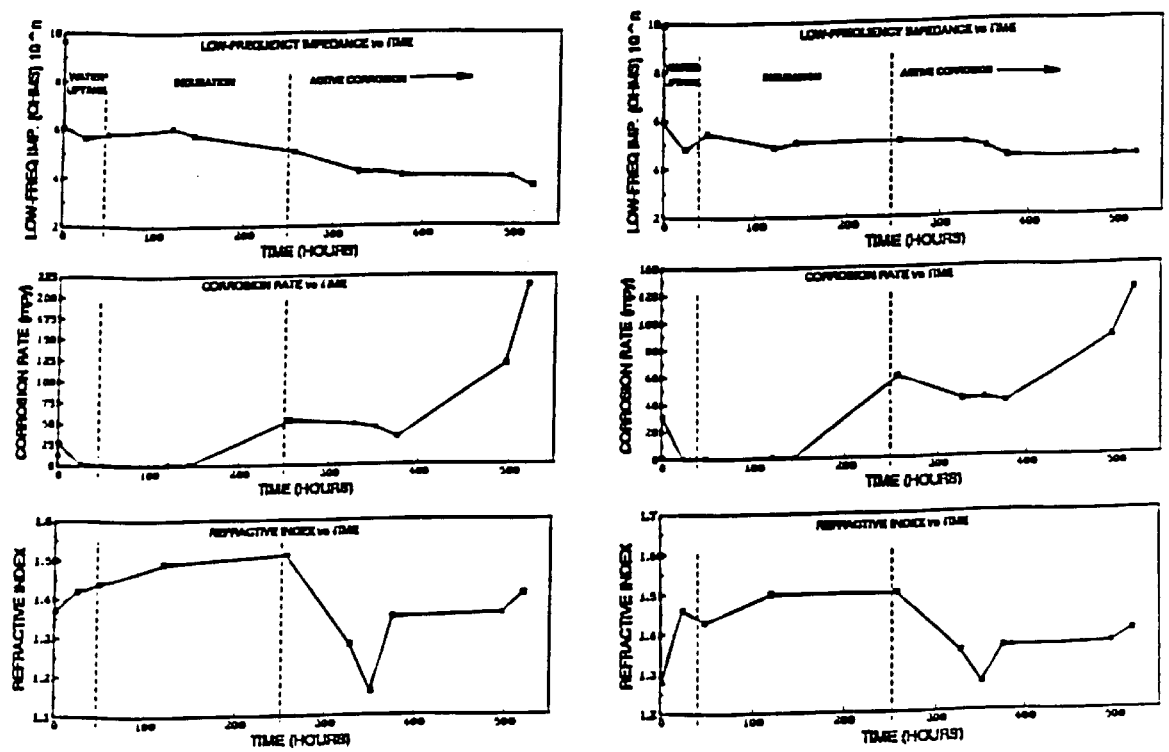

FIG. 12 shows plots of results from testing of scribed electrode-less aluminum 2024-T3 samples which were immersed in a 5% NaCl solution for the extent of the testing. The results for the sample with the epoxy polyamide primer is on the left and the results for the sample with the waterborne epoxy primer is on the right.

Figure 13:
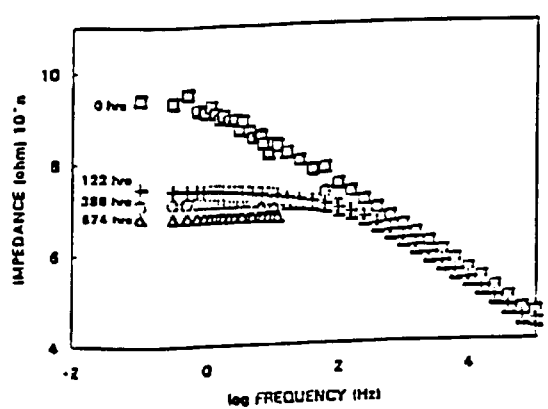
Figure 13:
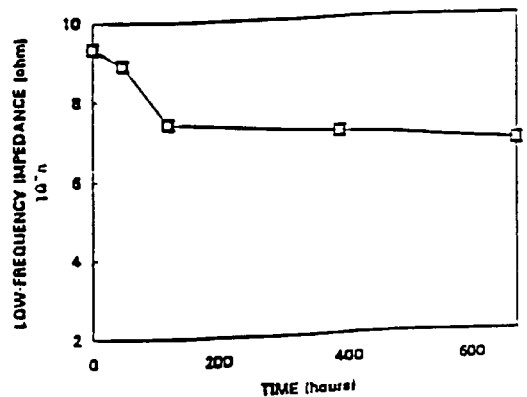

FIG. 13 shows plots of AC impedance results from salt spray testing of aluminum 2024-T3 samples coated with epoxy polyamide primer. The left graph displays impedance spectra at various exposure times while the right graph shows the low frequency impedance response (corrosion curve) to exposure time.

Figure 14:
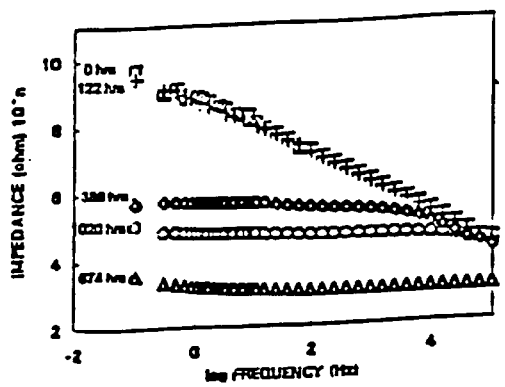
Figure 14:
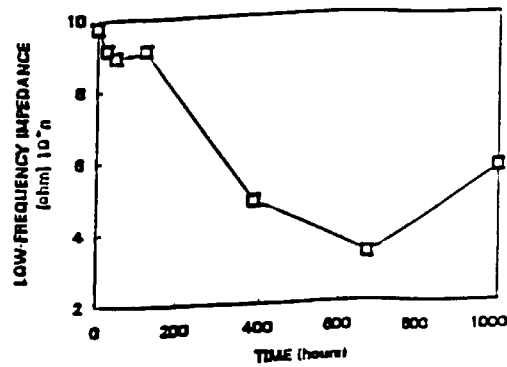

FIG. 14 shows pots of AC impedance results from salt spray testing of aluminum 2024-T3 samples coated with waterborne epoxy primer. The left graph displays impedance spectra at various exposure time. The right graph shows the low-frequency impedance response (corrosion curve) to exposure time. The last point of the right graph has a higher impedance due to drying of the specimen prior to the measurement.

Figure 15:
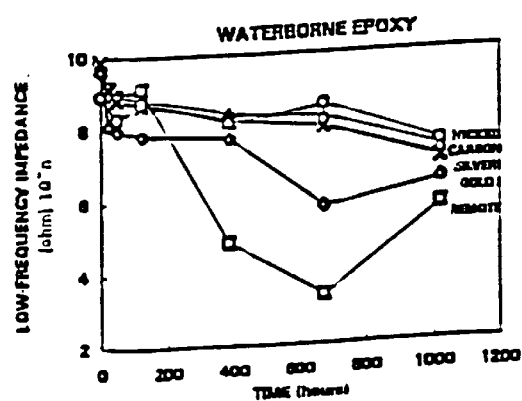
Figure 15:
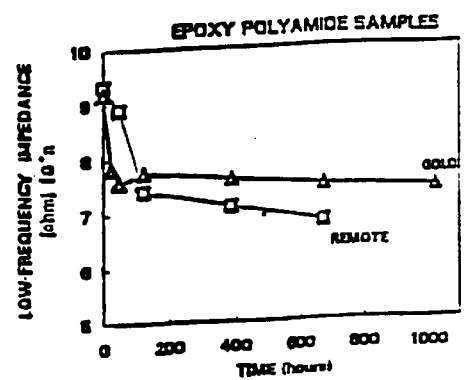

FIG. 15 shows plots of overlays of AC impedance results of two-electrode samples and conventional three-electrode remote samples from salt spray testing of aluminum 2024-T3 samples coated with epoxy polyamide primer and waterborne epoxy primer.

Figure 16:
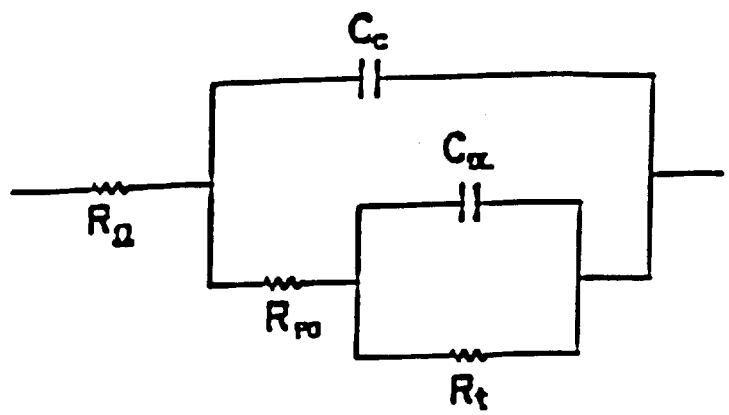

FIG. 16 is a diagram of an equivalent circuit model of a coated metal $R_o$ represents the solution resistance. $R_{po}$ and $C_c$ correspond to the coating, while $R_t$ and $C_{dl}$ correspond to the metal interface.

Figure 17:
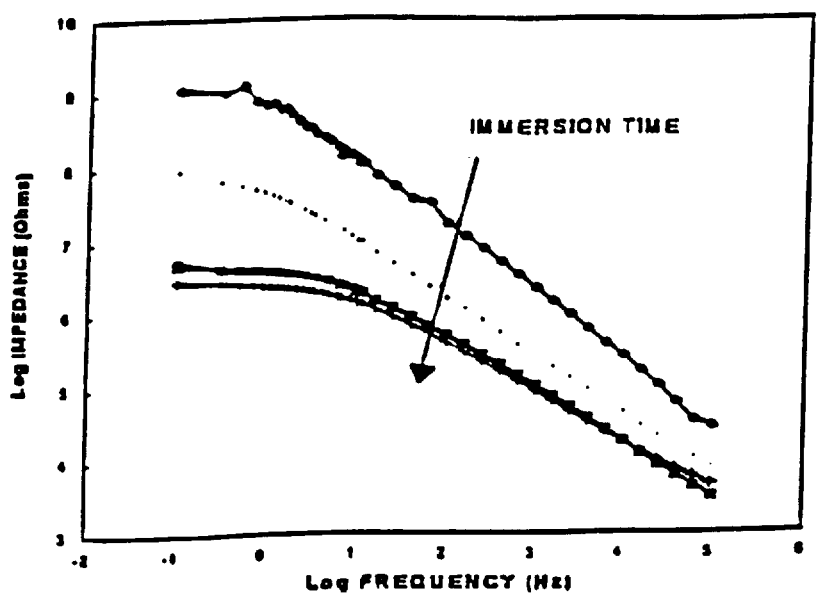

FIG. 17 shows plots of impedance spectra for painted aluminum following immersion of different periods in salt water.

Figure 18:
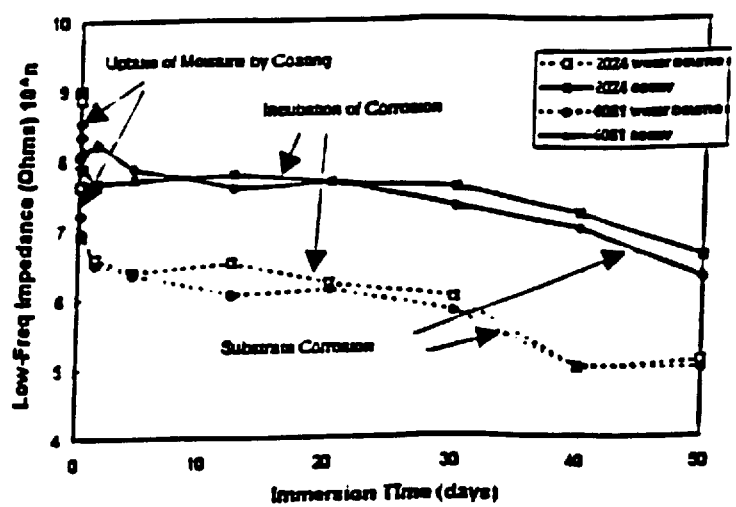

FIG. 18 shows plots of impedance versus immersion time for waterborne and epoxy polyamide paints on two different alloys of aluminum in salt water.

Figure 19:
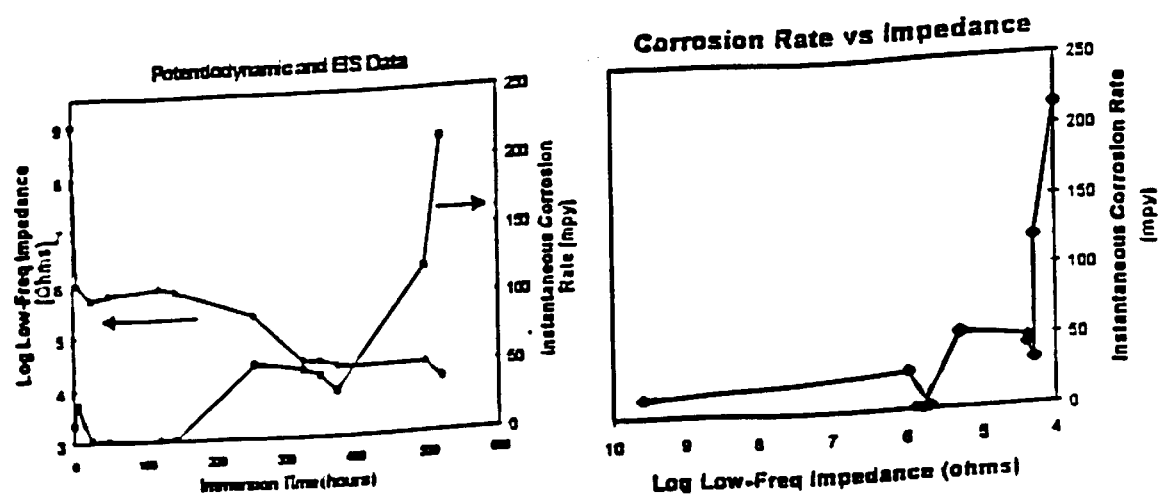

FIG. 19 shows (left) the near-dc (low frequency) impedance spectra as determined by the corrosion sensor and instantaneous corrosion rates as determined by potentiodynamic polarization as a function of time for painted aluminum in salt water. Right diagram is a plot of the corrosion rate as a function of near-dc impedance.

DETAILED DESCRIPTION OF THE INVENTION

INTRODUCTION

The AC Impedance technique, also known as Electrochemical Impedance Spectroscopy (EIS), is a nondestructive technique that is capable of monitoring and detecting the deterioration of organic coatings. EIS can evaluate coating degradation by determining a number of fundamental parameters related to the electrochemical kinetics of coating degradation. EIS has been used by numerous investigators to monitor coating deterioration.

Grandle and Taylor (1994)[1] have used EIS to examine the corrosive behavior of coated aluminum beverage cans. The study focused on determining a performance parameter obtained from the impedance spectra. Three parameters—coating capacitance, pore resistance, and low-frequency impedance—were examined. The results indicated that the low-frequency impedance was the optimal parameter.

Simpson et al. (1990)[2] have used EIS with an atmospheric electrochemical monitor to detect organic coating degradation in the atmosphere. The monitor was used successfully to generate EIS data that correlated well with near dc impedance and tensile adhesion strength.

Figure 1:
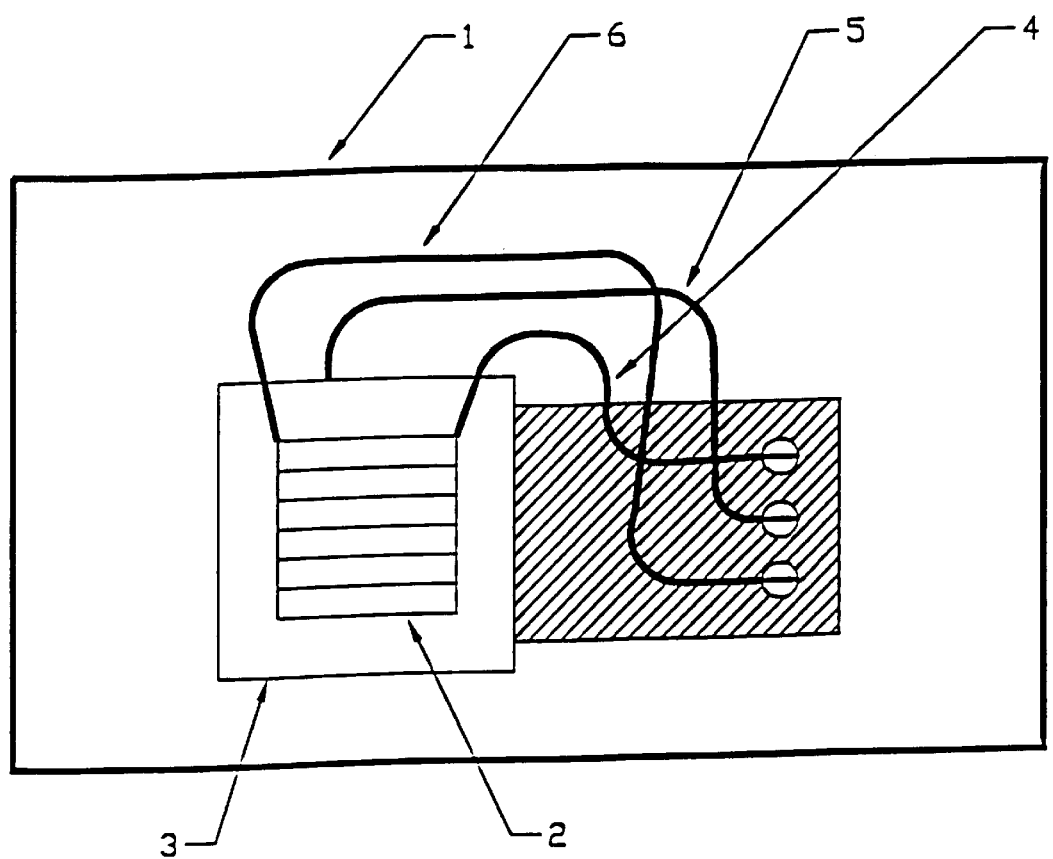
Figure 2:
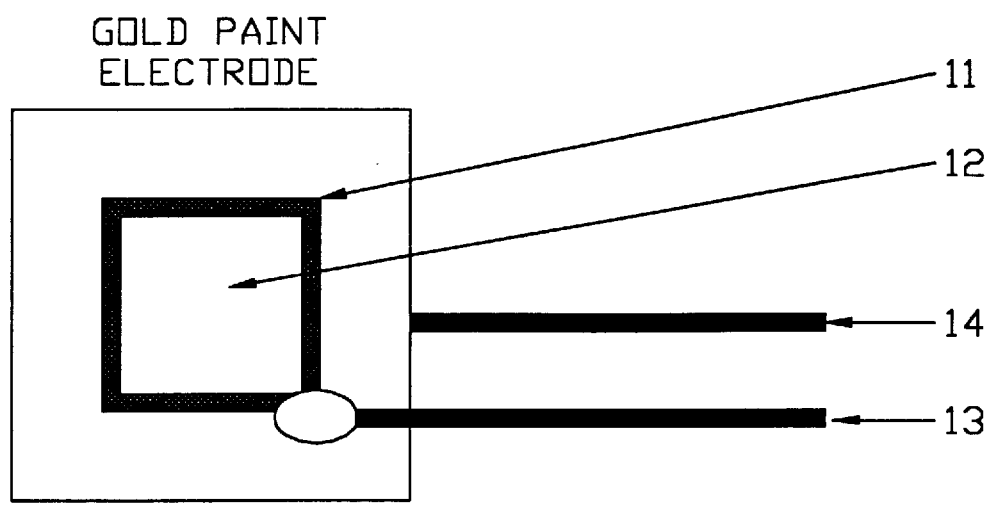
Figure 3:
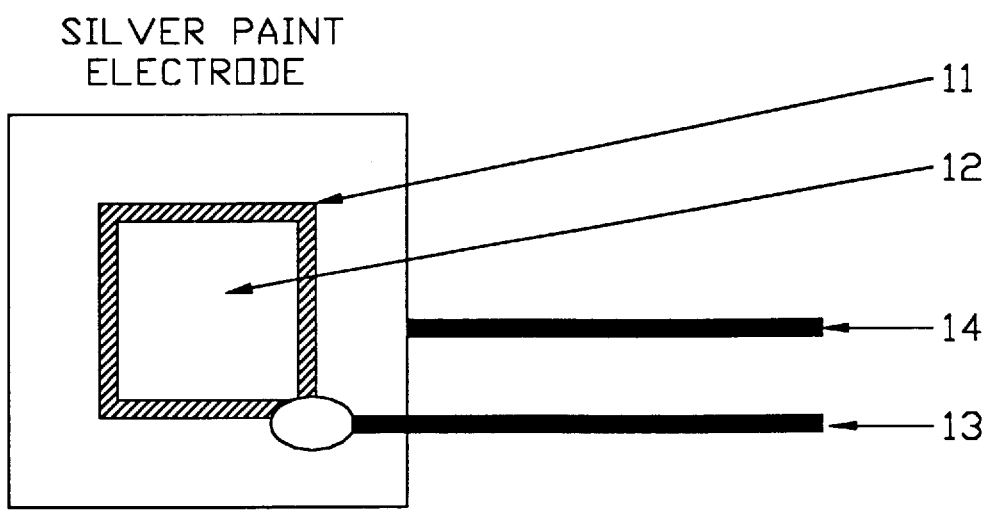
Figure 4:
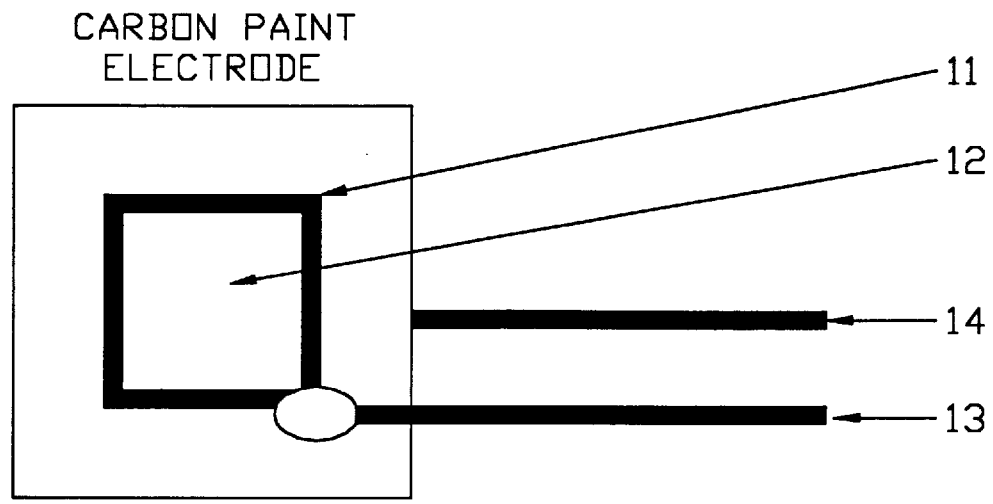
Figure 5:
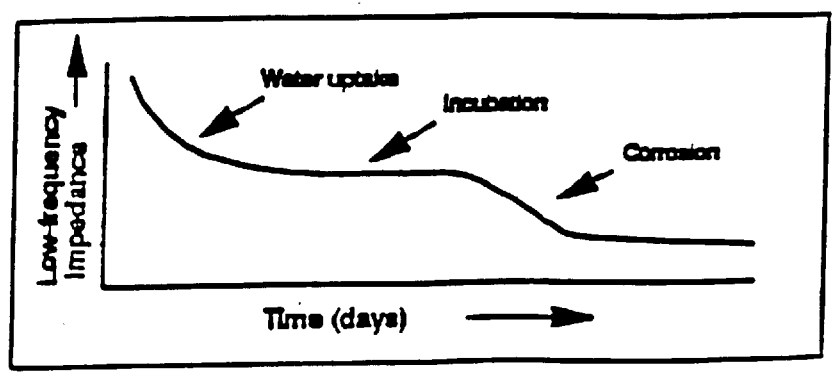

We set out to develop an in-situ sensor similar to Simpson et al. that was capable of detecting the corrosion on painted aircraft aluminum 2024-T3. EIS, ellipsometry and DC polarization techniques were used to define the extent of the corrosion process of the painted aircraft aluminum 2024-T3. Testing show that the painted aircraft aluminum 2024-T3 does degrade with a distinct signature which corresponds to the following plot in FIG. 5. There are definite regions on the corrosion spectrum showing water uptake, incubation, and intense corrosion activity. Phase I has proven the feasibility of using the AC Impedance technique to recognize the distinct degradation pattern for aircraft materials.

DACCO SCI, INC has developed several versions of prototype electrode sensor. Conventional AC Impedance testing requires the use of three electrodes and an electrolyte making in-situ analyses difficult to perform. Our two-electrode approach eliminates the need for an electrolyte and enables reliable in-situ real-time analyses of aircraft metal/coating systems.

The prototype sensor electrodes have a conductive ink (gold, silver, nickel, or carbon) deposited onto the coating. The use of the conductive ink on the surface of the coating eliminates the need for a counter electrode since the impedance of the conductive ink is much less than that of the coating. The conductive ink is applied directly to the surface of the coating, resulting in the conductive ink/coating interface having a much lower interfacial impedance as compared to the metal/coating interface. This allows the entire surface of the conductive ink to be utilized as the reference electrode. Electrical contact is made to the bare aluminum on the backside of the coupon as the working electrode. The result is a valid two-electrode electrochemical cell. The electrode can be a portable type or a blanket type laid on the surface of the metal structure.

These prototype sensors have been used to acquire EIS data in order to characterize the organic coating degradation. This functioning electrode sensor will greatly enhance the safety and decrease the service costs of the aircraft.

EXPERIMENTAL

Preparation of Samples

All sample coupons were prepared from a sheet of aluminum 2024-T3 (3' by 4' by 1/32") obtained from C-S Metals Service, Inc. The Al 2024-T3 sheet was then machined into sample coupons (1 by 1 by 1/32 in.) by Adams Machine and Tool Shop. The samples were coated with Mil-P-23377 Epoxy Polyamide Primer and Mil-C-83286 Urethane Topcoat, and half with Mil-P-85582 Waterborne Epoxy Primer and Mil-C-83286 Urethane Topcoat.

Choice of Conductive Epoxies and Inks for Electrode

Gold epoxy (Epo-tek, Inc.) was the obvious first choice for use as an electrode. Gold has excellent electrical conductivity and has a high resistance to corrosion. The major drawback of the gold epoxy is the cost. Carbon ink was used to provide a low cost alternative to the gold paint. Even though the electrical conductivity is less than that of the gold paint, the carbon paint still has a much greater conductivity compared to the coating to which it will be applied.

Silver ink and nickel conductive epoxy were added to the scope of testing to provide more low-cost alternatives to the gold epoxy since there was concern that the carbon conductive ink might not give accurate results due to its low electrical conductivity and suspected low abrasion resistance. The nickel conductive epoxy, in addition to its high electrical conductivity, has excellent resistance to abrasion.

A strip of each conductive ink was deposited onto a sample to measure the electrical resistance of each conductive ink. Each strip was one inch in length and 1/8" in width. The electrical resistance was measured from the endpoints of each strip. The results are shown in Table 2.

TABLE 2

| CURRENT RESISTANCE OF CONDUCTIVE INKS | | |
|---|---|---|
| Electrode Paint | Cure Temp. (°C.) | Resistance (Ohms) |
| Gold (Au) | 50 | 4.5 |
| Gold (Au) | 80 | 2 |
| Silver (Ag) | 50 | .4 |
| Nickel (Ni) | 50 | 1 |
| Carbon (C) | 50 | 675 |

It was found that the current resistance of the gold epoxy decreased with cure temperature as supported by the specification sheet sent with the epoxy. However, there was concern that elevated cure temperatures might adversely alter the integrity of the coating. Therefore, the lowest possible recommended cure temperature of 50° C. was chosen for all the paints. The lowest possible cure temperature is also more practical for field application of the conductive paint electrodes.

Application of the conductive paint electrodes did not appear to alter the coating surface, with the exception of the gold epoxy paint, which subtly changed the appearance of the paint coating on both types of coating systems. This was verified both visually and with the ellipsometer, in which, no changes in the refractive index were observed after the application of the electrode.

Preparation of Samples with Electrodes

Cleaning of Painted Surface.

The coated surface of each sample (11) was rinsed with isopropyl alcohol (IPA) from a rinse bottle while held with tweezers in a lower corner. Rinses were performed until no surface streaks or spots were observed. The panels were handled with clean gloves and tweezers during and after cleaning.

Masking of Painted Surface.

An outer frame of dimensions 1"×1" was constructed of 3M #658 Post-it correction tape. A square with sides of 17/32" was cut out of the middle of this frame with sides parallel to the outside sides. From a different piece of the 3M tape another square piece was cut with sides measuring 15/32".

The electrodes (12) were formed by painting conductive epoxies and inks onto the panels through the gap in the tape mask using a very small brush, which was cleaned with IPA when switching to another conductive epoxy. The painted electrodes were allowed to dry at room temperature for at least thirty (30) minutes and then the frame was removed.

Application of Wires to the Electrode and Sample.

The wires (13, 14) were stripped of their insulation and the exposed metal was cleaned with IPA. One wire (13) was attached to the electrode (12) by laying it into a pool of the conductive silver 2-part epoxy in contact with the epoxy coating on the top side. After curing at room temperature for thirty minutes, the samples were placed in the oven to cure at 50° C. for 20 hours. 3M 1838 B/A two part epoxy adhesive was then applied on the surface of the silver epoxy used to bond the wire for the purpose of providing additional strength and protection to the bond.

Application of Glyptal to Sample.

Glyptal was applied to all exposed aluminum surfaces including edges and the backside of each sample. Glyptal provides a coating to the bare aluminum and prevents the aluminum from absorbing any water through the sides and back of the sample. Therefore, water can only be absorbed through the coating, similar to that which occurs on an aircraft coating.

Scribing of Samples.

Figure 6:
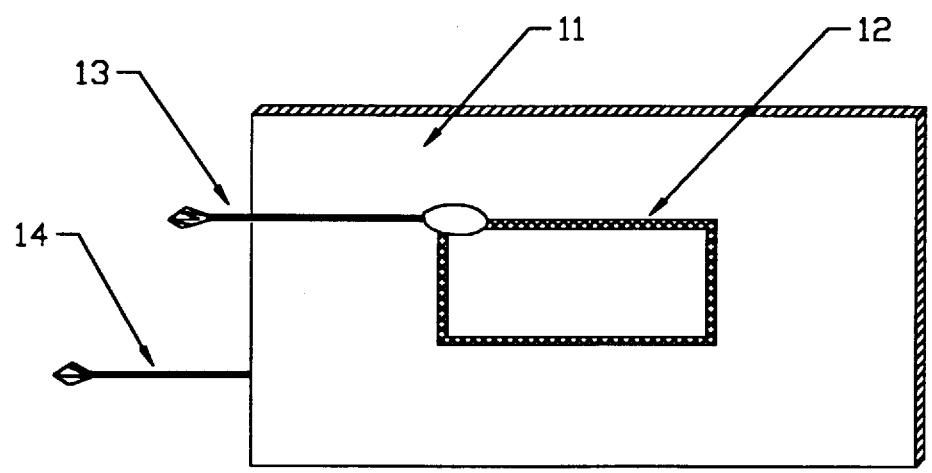

Several batches of electrodes were scribed in order to perform salt fog testing and corrosion testing. Scribing was performed according to ASTM D 1654-79a. Two one (1) centimeter lengths inside the electrode area were scribed in the shape of an "X" with the aluminum substrate being exposed. FIG. 6 displays a drawing of a sample (11) with a conductive ink deposited as an electrode (12).

Electrode-less (Remote) Sample.

Samples that were used to perform three-electrode AC Impedance testing did not have an electrode deposited on the surface. These samples were used to compare electrochemical results with the two-electrode approach. These samples are referred to as electrode-less or remote samples.

Electrochemical Testing AC Impedance Technique.

Electrochemical impedance spectroscopy was performed on the machined samples using the EG&G Princeton Applied Research Potentiostat Model 273. An EG&G Lock-in Amplifier Model 5210 was used in order to generate the alternating current waveform. EG&G Model 398 version 1.10 Electrochemical Impedance software was used.

The EG&G K0235 Flat Cell electrochemical cell was used to verify results obtained from the painted electrodes. A 250 Ml 0.05 Molar $Na_2SO_4$ solution (pH=6.05) was used as the electrolyte. The corrosion cell requires the use of an electrolyte and a counter electrode. Three electrical connections are made using the corrosion cell. A working electrode was connected to the backside of the sample. The reference electrode was connected to a Silver/Silver Chloride electrode to measure the current. The third connection was for the counter electrode.

Painted electrodes were tested without the use of an electrochemical corrosion cell. The electrodes were connected directly to the potentiostat. The working electrode was connected to the metal backside of the sample. The reference electrode was electrically connected to the painted electrode. The counter electrode was left unconnected.

DC Potentiodynamic Scans.

The EG&G Model K47 Corrosion Cell System was used to perform potentiodynamic scans on the samples in order to calculate corrosion rates. A 0.05 Molar $Na_2SO_4$ solution was used as the electrolyte. The samples were immersed completely in the electrolyte and electrically connected as the working electrode. Reference (saturated Calomel electrode) and counter electrodes were used. DC current was then sent through the sample to induce corrosion which was then measured using the EG&G Model 352 SoftCorr II Corrosion Measurement and Analysis Software.

Ellipsometry

Ellipsometry was conducted using the Gaertner Scientific Model L119x Ellipsometer using a 4 mW Helium-Neon laser with a wavelength of 6238A. A flat panel holder was used to hold the samples and perform optical measurements. The laser light passed through the quarter-wave plate and on the sample. The light was then reflected off the coating and into the photocell. Gaertner Scientific GS-SC4A L104 software package automatically controlled the photocell and determined the null point. The index of refraction, the coefficient of extinction, Psi, and Delta were then calculated.

Salt Fog Testing

Salt spray testing was conducted using the Singleton Corporation SCCH Corrosion Test Cabinet Model 20. A 5% NaCl solution at 99° F. was used for salt fog testing (ASTM B117).

X-ray Photoelectron Spectroscopy (XPS)

XPS characterization was performed using the Surface Science Instruments SSX-100 system with a torodial crystal monochromatized Al x-ray source.

RESULTS

Testing was then performed to characterize the virgin samples. Initial testing was followed by design of electrode sensors capable of obtaining impedance spectrum. Samples (with and without electrodes) were tested using electrochemistry, ellipsometry, salt spray and immersion testing.

Initial Testing of Samples

After being coated, two samples (one with waterborne epoxy primer and the other with epoxy polyamide primer) were photomicrographed in order to analyze the appearance of the coating surface. Both specimens were very uniform in appearance, even though several small defects were documented on each specimen. This was verified with the ellipsometer, where it was determined that both metal/coating systems displayed identical refractive indices at various locations on the sample. This was anticipated, since both have an identical urethane topcoat. The surface of either sample was not entirely smooth (free of defects) but still simulated the typical surface of an aircraft. Furthermore, XPS was used to characterize the constituents of the urethane topcoat.

Figure 7:
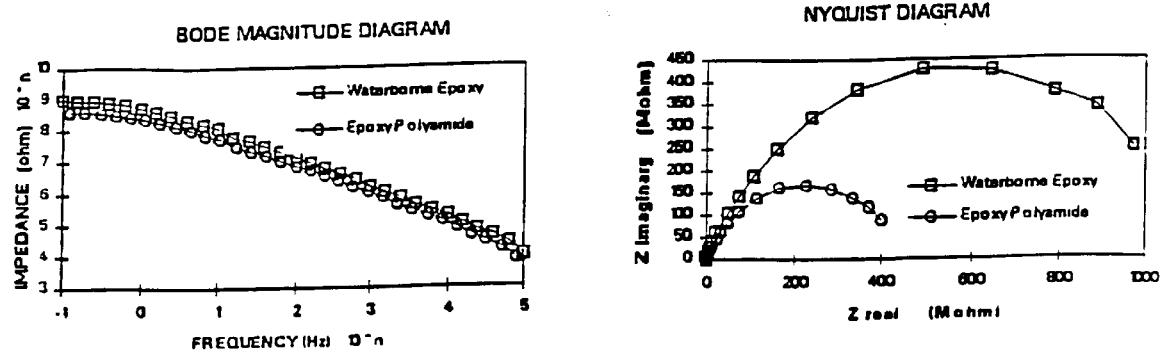
FIG. 7 is a plot of samples that underwent AC impedance testing in a conventional three-electrode corosion cell to obtain the Bode and Nyquest diagrams from testing of aluminum 2020-T3.

Several samples without electrodes underwent AC impedance testing in a conventional three-electrode corrosion cell to obtain initial impedance spectra (FIG. 7). Analysis of the spectra revealed that the aluminum 2024-T3 coated with the waterborne epoxy primer displayed larger impedance values than the epoxy polyamide primer at all frequencies. This was confirmed from analysis of the Nyquist plot of both primers where it is evident that the waterborne epoxy exhibits larger real and imaginary impedance values than the epoxy polyamide. This preliminarily indicated that the samples coated with waterborne epoxy primer had a higher resistance, were more thickly coated, or absorbed less water than those coated with the epoxy polyamide primer. A thicker coating and less water absorption are both likely to correlate with an increased corrosion resistance.

AC Impedance Testing

Figure 8:
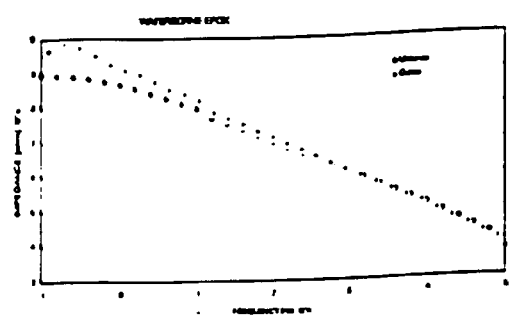
FIG. 8 is the Bode plots of impedance spectra for cured and uncured using the three (3) electrode method.
Figure 8:
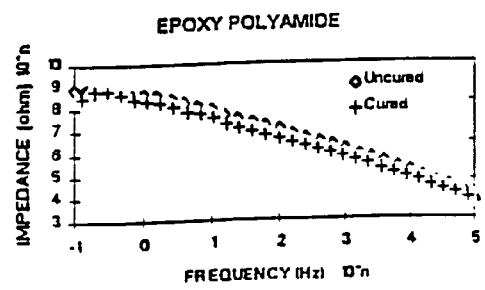

AC impedance testing was then conducted on the electrode sensors to quantify any differences in impedance spectra obtained previously from the three-electrode method on samples without the electrodes. It was found that the impedance was much higher, approximately one order of magnitude for both primers, after the electrodes were applied to the coating (FIG. 8). It was determined that the difference in the overlays was due to the curing of the painted electrodes on the specimen. The curing of the electrodes at 50° C. for 20 hours evaporated all solvents and water that were located within the coating. In the time it took to get the samples back from being professionally coated, the samples had experienced an initial water uptake which was measured and quantified using the AC Impedance technique. The curing process increases the impedance of the coating and represents a reproducible baseline reference.

Figure 9:
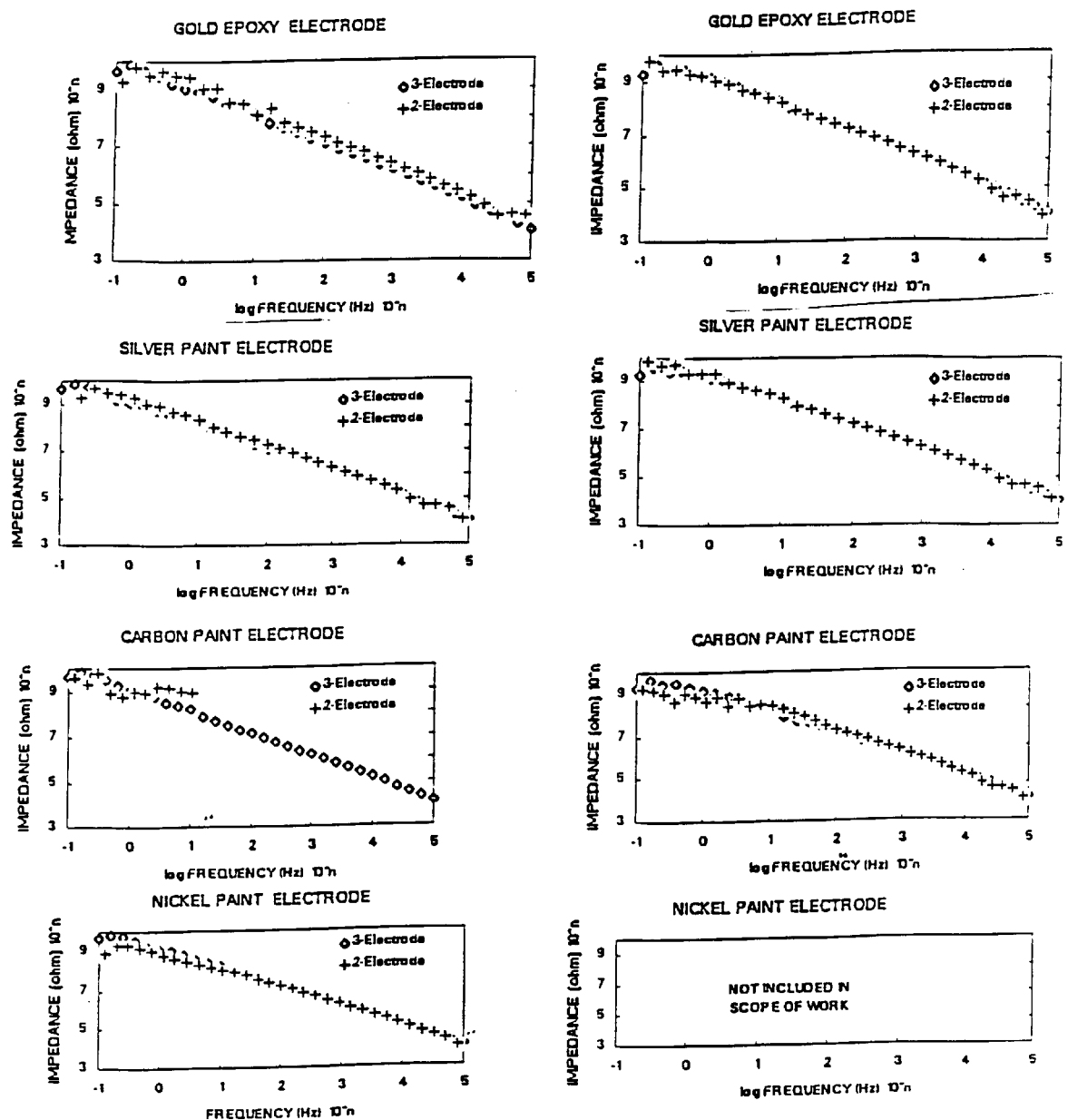
FIG. 9 is a two (2) electrode impedance spectra for conductive inks on aluminum 2024-T3 samples coated with waterborne epoxy primer and epoxy polyamide primer overlaid with three (3) electrode spectra from electrode-less samples.

Based on this information, AC impedance spectra were obtained for cured electrode-less samples using the three-electrode method and overlaid with the spectra for the conductive paint electrode sensors using the two-electrode approach (FIG. 9). The gold, silver, and nickel conductive paint electrode results show a remarkable overlay with the three-electrode electrode-less spectrum. Some of the carbon electrodes had difficulty reproducing the impedance spectrum of the baseline. These discrepancies in results for the carbon paint electrodes could be due to its lower electrical conductivity or to a process in which the graphite particles become surrounded and isolated by the epoxy polymer and result in a higher impedance than would be expected. The well behaved carbon electrode suggests that this may be a solvable problem. Variables such as the cure temperature, the starting viscosity, and the amount of paint applied could be adjusted to increase the electrical conductivity.

Verification of Impedance Results Intentional Defect—Immersion Test

To study coating degradation, an intentional defect was introduced in to a batch of samples. A model (21) of the test sample (11) with an intentional defect (15) is shown in FIGS. 10 and 11. The scribe (15, 22) initially penetrates through the entire oxide layer (25) to the aluminum substrate (26). However, instantaneous oxide growth occurs so the aluminum substrate (26) is never in direct contact with the electrolyte. A series of tests were performed on samples with and without conductive paint electrodes to track the water uptake, incubation, and corrosion of the aircraft coating using the AC Impedance technique. The testing was performed in order to correlate the low-frequency impedance obtained using EIS with instantaneous corrosion rates and changes in the refractive index of the coating. Samples were immersed in a 5% NaCl solution when not being tested. Each of the samples underwent the following tests along with visual observation each day of testing: 1) a DC potentiodynamic scan to measure the instantaneous corrosion rate, 2) an ellipsometric test to measure the refractive index of the aluminum substrate, and 3) an AC Impedance test to obtain the impedance spectrum and monitor the low-frequency impedance response. In FIG. 11, layer (3) represents the urethane topcoat and layer (4) the primer.

The results indicate good correlation between the three tests as seen in FIG. 12. Both the waterborne epoxy primer and the epoxy polyamide primer samples display similar plots of low-frequency impedance vs time which is characteristic of the corrosion process for aircraft metal/coating systems. The act of scribing the samples drops the low-frequency impedance by four orders of magnitude. The corrosion rates of the samples 'jump' to a peak just after the scribing has occurred. This is anticipated since the bare aluminum substrate is now exposed to the atmosphere. The corrosion rate then returns to a lower rate as a protective oxide immediately begins to form on the exposed substrate.

The results for the two aircraft metal/coating systems are quite similar. Both experience the same relative corrosion process according to the plot of low-frequency impedance versus time. It is apparent that the waterborne epoxy primer is slightly more resistant to corrosion than the epoxy polyamide primer. At the onset of corrosion, the epoxy polyamide experiences a sharper decline in low-frequency impedance and levels off at around 8,000 ohms. The waterborne epoxy at the onset of active corrosion has a more gradual decline in low-frequency impedance and levels off at a larger low-frequency impedance of around 25,000 ohms. Even though the scribe for both metal/coating systems penetrated to the substrate, the waterborne epoxy sample was able to resist corrosion more effectively. This was most likely due to the better ability of the waterborne epoxy primer to resist the ingress of water and ions into the surrounding defect area of the scribe, resulting in larger low-frequency impedance values.

The process of scribing the samples to induce corrosion bypassed the bulk of the water uptake stage of corrosion. If the samples had not been scribed, it would have been possible to monitor the water uptake of the samples until the incubation stage was reached. However, an extended amount of time is needed for the coating to absorb enough water to reach the incubation stage.

Further analyses of the water uptake stage was later performed using AC Impedance in conjunction with salt fog testing.

The results from the ellipsometer indicate that definite changes occurred in the refractive index of the samples throughout the testing. The refractive index is a measure of the dispersion of the reflected light traveling through the scribed sample. The presence of the scribe damage and the resulting oxide growth has been detected. As with the impedance of the coating, the refractive index drops sharply after the scribing, indicating less dispersion of the reflected light due to the exposed aluminum substrate. The refractive index became larger again as the oxide formed. While it is difficult to directly compare the impedance and the refractive index, the plot shows that changes in the low-frequency impedance data respond well to the changes in the refractive index. Soon after the scribing, approximately 40 hours, the samples entered the incubation period. This stage characteristically has a constant low-frequency impedance. The samples experienced an ingress of water and ions deeper into the defect and surrounding pores. This was verified by the near constant corrosion rates measured during this stage. Likewise, the refractive index slightly increased over the incubation stage as the ingress of water and ions altered the contour of the sample surface. This resulted in greater dispersion of the reflected light. Visual observation of the defect area revealed that the aluminum substrate showed no signs of discoloration or corrosion.

After 250 hours of immersion, the samples began to experience active corrosion. At the onset of active corrosion, the corrosion rate increased dramatically from around 2 milli-inches per year (mpy) to over 50 mpy and, correspondingly, the low-frequency impedance began to drop about 2 orders of magnitude. At this point, visual observation of the defect area revealed that the aluminum substrate had become slightly discolored and had lost some luster. After the initial spike in the corrosion rate, the corrosion rate then leveled off at around 40 mpy before again increasing rapidly to over a 100 mpy for the waterborne epoxy and 200 mpy for the epoxy polyamide. The refractive index begins to drop at the onset of corrosion which indicates that the corrosion has less dispersion due most likely to an initial even oxide growth. By the end of the testing, the refractive index was increasing in response to the accelerated corrosion producing uneven oxide growth. At the end of the immersion testing, the defect area was visibly corroded. The samples with the conductive paint electrode sensors showed no signs of the electrode grid de-adhering from the topcoat. The gold and carbon electrode grids showed no visual signs of degradation. The silver grid, however, had discolorations on the inside part of the grid possibly due to the ingress of the NaCl solution into the silver paint.

The use of the conductive paints to track the paint water absorption from a scribe suggests the value of further development and optimization of the electrodes. The two-electrode measurements did not indicate a drop in impedance as seen by the three-electrode measurement of the electrode-less sample. The three-electrode method on the electrode-less samples measures the impedance along the lowest resistivity path between the electrode and the aluminum alloy. Thus, a scribe tends to completely short-circuit the paint on the aluminum with direct electrolyte to metal contact. The painted electrodes measure the impedance through the paint medium to the metal. As a result, a scribe contributes to a decrease in impedance only insofar as a surface conductive path exists between the conductive paint electrode across the paint to the metal. Aside from this possible contribution, it is necessary for the underlying corrosion of the metal surface to change the impedance of the paint itself by producing ionic conduction through the paint. This does not happen until the metal oxidization process dominates the formation of passive oxides. Thus, the decrease in conductive paint electrode impedance is expected to lag behind that of the electrode-less specimen.

Salt Fog Testing

Salt spray testing was conducted in order to determine: 1) the ability of the painted electrodes to withstand harsh environments for extended exposure times, 2) the corrosion process of waterborne epoxy and epoxy polyamide primed samples without the use of a scribe, and 3) the ability of the painted electrodes to track the corrosion process.

The use of the salt spray cabinet afforded a chance to accelerate the corrosion process of the samples without the need to introduce an intentional defect. This testing enables the painted electrodes to measure the impedance of the coating more accurately than if a scribe was present. After 1,020 hours of exposure, none of the electrodes (gold, silver, carbon, or nickel) showed any signs of losing integrity or de-adhering from the topcoat. In fact, the electrodes outlasted the glyptal coating applied to the backside of the samples. All samples prepared for the salt spray testing were given one heavy coat of glyptal to the metal backside and the edges of the samples. Due to the harsh environment of the salt spray, the glyptal began to peel back from the edges and blister. This exposed tiny avenues for salt spray penetration to the exposed metal backside. This resulted in corrosion products forming on the backside of the coupon and possibly creating larger impedance drops than anticipated. Testing procedure at this point was changed in order to alleviate the situation. Each sample was immediately rinsed and dried off with nitrogen and allowed to dry at ambient for at least thirty minutes. This resulted in a rise in impedance values of the specimens tested after 674 hours.

The results are consistent with data obtained from the immersion testing. Impedance spectra of the electrode-less remote electrode epoxy polyamide samples and the resulting low-frequency impedance vs. time corrosion curve is given in FIG. 13. After about 122 hours of chamber exposure, the impedance drops about 2 orders of magnitude and, thereafter, continues a slow decrease in impedance for the remainder of the test. The resulting corrosion curve shows the initial drop (water uptake), before leveling off in the incubation period. It appears that after 674 hours of exposure, the sample did not enter the active corrosion stage. This was confirmed from visual observation, in which both the electrode and the coating appeared unchanged. Testing would have continued except for the fact that the electrode wire detached from the test specimen after 1,020 hours of exposure due to penetration of the salt spray.

Salt spray results for the remote waterborne epoxy sample are shown in FIG. 14. The waterborne epoxy sample displays a greater resistance to water uptake than the epoxy polyamide sample and does not drop in low-frequency impedance until 386 hours of exposure, unlike the 122 hours of exposure for the epoxy polyamide sample. These results are consistent with the immersion testing, in which, the waterborne epoxy resisted water ingress into the surrounding defect area of the coating better than the epoxy polyamide sample. After the initial water uptake, the impedance drops approximately four orders of magnitude before again increasing at 1,020 hours of exposure, most likely due to the change in testing procedure. No significant decline in impedance during the incubation stage was observed, indicating that the remote sample did not enter the active corrosion region. This was supported by visual observation of the topcoat.

FIG. 15 displays the AC Impedance testing results comparing the conductive paint two-electrode approach with conventional three-electrode remote testing. All the conductive paint electrodes for both primers show the ability to monitor the corrosion process, showing well-defined regions of water uptake and incubation corresponding to the conventional three-electrode results from the electrode-less remote samples. The gold electrode had an excellent overlay with the remote sample for both the waterborne and epoxy polyamide samples. The nickel, carbon, and silver electrodes have similar results, but display larger impedance values during the incubation stage than the remote sample. Variables such as the amount of penetration of salt spray and resulting corrosion products on the backside of coupons appear to have contributed to the differences in the overlays.

CONCLUSIONS

In-situ electrode sensors capable of sensing coating degradation using the AC Impedance technique have been designed and tested. The electrode sensors have been used to generate two-electrode EIS data equivalent to data obtained using the conventional three-electrode method. Furthermore, equivalent EIS results have been obtained in aggressive environments including immersion and salt fog testing. Results from the chamber-exposed electrode sensors indicate that coating deterioration is a function of exposure time. EIS results were verified through the use of ellipsometry and DC potentiodynamic scans which correlated the amount of corrosion with near-DC low-frequency impedance values. This correlation of results indicates excellent predictive capabilities of the two-electrode sensors using the AC Impedance technique. The research has identified and developed analytical techniques to detect coating degradation at early exposure times. These in-situ electrode sensors and their potential applicability for nondestructive, real-time analysis of coating degradation represent an opportunity to develop an uncomplicated straightforward commercial sensor which will ultimately reduce maintenance and downtime.

Electrochemical impedance spectroscopy (EIS) has been used to detect coating degradation on steels and other metals. Very good correlation has been reported between short-term EIS data (Low frequency [near-dc] impedance and break-point frequency) and long-term coating performance demonstrating the technique's predictive capabilities. Aluminum alloys with common aircraft coatings have been examined by EIS with excellent correlation with other techniques of evidence of corrosion.

The in-situ corrosion sensor using EIS offers a quantitative measure of incipient corrosion unlike other corrosion monitors that simply measure the time of wetness or the corrosion rate of the sensor itself or that require external electrodes and bulk electrolyte medium. As such, it is directly applicable to detect the degree of coating degradation and the amount of substrate corrosion of real structures. Because it detects the very early stages of corrosion, it provides a warning before structure degradation occurs. Thus preventative maintenance can be scheduled in time to forestall corrosion damage.

Two version of the corrosion sensor have been developed:
  A portable hand-held instrument that a technician would press or hold against the structure.
  A painted sensor that would be applied to the structure permanently and then monitored at appropriate intervals with a technician equipped with a portable computer. Alternatively, the sensor (or an array of sensors) could be continuously monitored by a dedicated computer.

The in-situ corrosion sensor measures the impedance spectrum of a metal/coating system as a function of accelerated exposure. The metal/coating system is often modeled with an electric circuit such as that shown in FIG. 16. Initially, the coating resistance is very high (and the solution resistance is very low) so that the system acts as a capacitor with an log impedance-frequency slope of −1 (FIG. 17). As the coating degrades the substrate corrosion occurs, the resistance of the coating decreases and the lower branch of the circuit becomes important at low frequencies. The near-dc impedance then becomes independent of frequency.

The impedance spectrum can interpreted to precisely determine the stage of corrosion the metal/coating system is experiencing as illustrated in FIG. 18. The data have shown that the painted metals degrade with a distinct signature. There are definite corrosion stages corresponding to water uptake by the polymer, corrosion incubation, and intense corrosion activity. Furthermore, differences are readily observed between coatings of different effectiveness.

The use of ellipsometry and DC potentiodynamic measurements have verified the results obtained from EIS. FIG. 19 shows the correlation between corrosion rates and near-dc impedance as measured by the sensor. For this system, corrosion rates are small until the near-dc impedance decreases to below $10^5$ ohms.

Two versions of the corrosion sensor are being developed that are suitable for monitoring different structures. One is an incorporated electrode that is permanently attached to the structure. This version is especially useful for inaccessible locations. Wires are then routed to a convenient connection point. Alternatively, wireless remote interrogation of the sensor is feasible. The other version is a portable hand-held electrode that is pressed against the structure during the measurement. This version could be used whenever a permanent electrode had not been incorporated into the structure. Laboratory measurements have indicated that the two sensor configurations give identical results. In both cases, measurements can be obtained using commercial portable equipment.

Investigations of the in-situ corrosion sensor showed:
  The measurements are identical with those obtained using remote electrodes. This assures that the methodology and analyses established for the conventional EIS measurements are suitable for the corrosion sensor results and that the successes established in conventional laboratory investigations of coated metals are expected with the corrosion sensor.
  EIS data correlates very well with corrosion rate measurements.
  The corrosion sensor is suitable for use in a variety of environments, including immersion, ambient, salt fog, humidity, and aggressive atmospheres.
  The sensor is suitable for a variety of metal substrates and coating chemistries. In particular, it has been demonstrated on 2024, 6061, and 7075 aluminum and cold rolled steel substrates and on epoxy, polyamide, urethane and alkyd primers/paints and epoxy adhesives. No limitation in the substrate or coating is anticipated provided the substrate is conductive and the coating is non-conducting.
  Differences in relative coating effectiveness are easily observed.
  The sensor detects very early stages of paint degradation and corrosion before any visual indications. This detection of corrosion before any structural damage has occurred is important. It potentially allows the health of the painted structure to be monitored so that maintenance can be scheduled on a needs basis instead of a fixed time interval basis.
  The sensor is capable of detecting coating defects away from the sensor itself. Laboratory measurements show that defects can be found up to fifteen feet form the sensor (The tested distance was limited by the size of the specimen.)

Identical results are obtained with the painted sensor and portable hand-held sensor suitable for spot inspection.

Comparison of Corrosion Sensors

| DACCO SCI, INC. Corrosion Sensor | Other Corrosion Sensors |
|---|---|
| ● Measures corrosion of actual structure | ● Time of wetness monitors |
| ● Sensitive to early stages of Corrosion/degradation | ● Corrosion of sensor itself |
| | ● Material differences |
| | ● Environmental differences |
| ● Very sensitive to moisture intrusion into bondline | ● Require significant loss of material (e.g., x-rays) |
| ● Relatively inexpensive instrumentation | ● Require delamination or blistering |
| ● Monitors electrochemical process (corrosion) directly | |

CITATIONS

1. J. A. Grandle and S. R. Taylor, "Electrochemical Impedance Spectroscopy of Coated Aluminum Beverage Containers: Part 1- Determination of an Optimal Parameter for Large Sample Evaluation," *Corrosion* 50, 792 (1994).
2. T. C. Simpson, P. J. Moran, H. Hampel, G. D. Davis, B. A. Shaw, C. O. Arah, T. L. Fritz, and K. L. Zankel, *Corrosion* (*Houston*), 46 (1990) 331.

We claim:

1. A method for the early detection of electrochemical corrosion, metal and coating degradation utilizing an inexpensive, in situ, and nondestructive electrochemical sensor, for detection of corrosion of coated metallic structures (e.g. bridges, aircraft, ground vehicles, storage tanks, buildings, or ships) comprising the steps of:

(a) providing an in situ sensor for producing an output correlative to an identifiable impedance spectrum (i.e., the impedance magnitude and phase as a function of the frequency of the applied voltage, created utilizing ac Impedance or Electrochemical Impedance Spectroscopy (EIS)) comprising a two electrode sensor responsive to atmospheric, water uptake, incubation, and corrosion to produce differences in impedance spectra utilizing, as one electrode, conductive ink deposited on the coating as a counter/reference electrode, eliminating the need for a remote or counter electrode by electrolyte immersion;

(b) applying a small electrical voltage between the metallic substrate of the structure as the working electrode and the counter/reference electrode and measuring the resulting current based upon the applied voltage between the electrodes;

(c) converting an analog signal indicative of the measured current to a corresponding ac impedance signal;

(d) providing a potentiostat's microcomputer with an operational program representative of a functional expression which correlates to distinctive impedance signatures; and (e) converting the impedance spectrum as a function of accelerated exposure and interpreting the said spectrum to determine the stage of corrosion the metal and/or coating has experienced.

2. The method according to claim 1, wherein said in situ sensor produces an output sensitive to differences in impedance spectra for a variety of materials and coatings by characterizing the constituents of an outer surface of a material and identifying structural degradation at an early stage.

3. An apparatus for detection of metal and coating degradation of a metallic structure or coupon based on an identifiable impedance spectrum (i.e. the impedance magnitude and phase as a function of the frequency of the applied voltage created utilizing ac impedance or Electrochemical Impedance Spectroscopy (EIS)) comprising:

(a) means for measuring impedance spectra by applying electrical voltage between the metallic substrate of the structure or coupon as a working electrode and a counter/reference electrode comprising conductive ink deposited on the coating and measuring the resulting small electrical current based upon the applied voltage between the electrodes;

(b) means for converting an analog signal indicative of the measured current to a corresponding ac impedance signal;

(c) a potentiostat's microcomputer with an operational program representative of a functional expression which correlates to distinctive impedance spectra; and (d) means for converting the impedance spectrum as a function of accelerated exposure and interpreting the said spectrum to determine the stage of corrosion the metal and/or coating has experienced.

* * * * *